Figure 1:
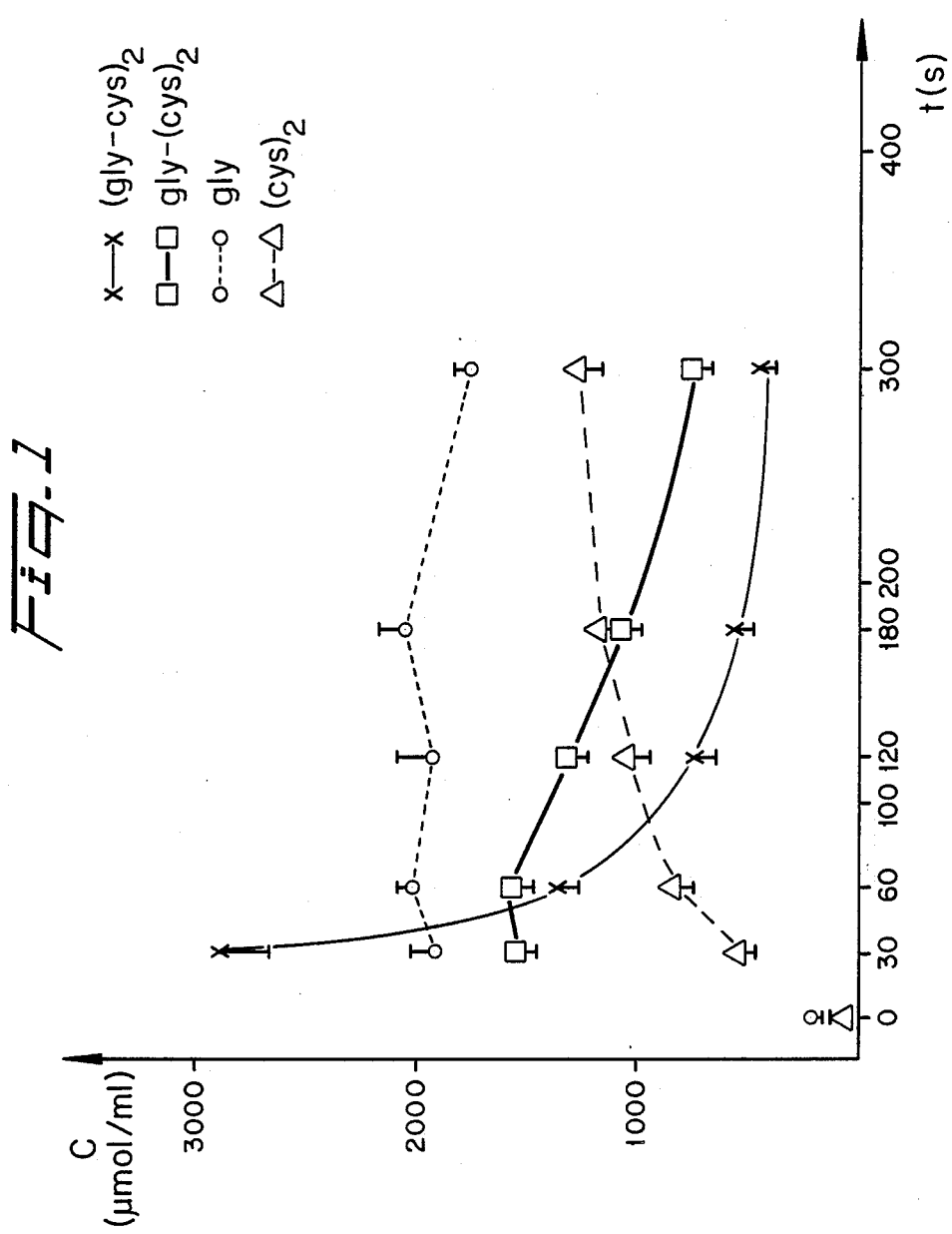

United States Patent [19]

Stehle et al.

[11] Patent Number: 4,968,696

[45] Date of Patent: Nov. 6, 1990

[54] N,N'-BIS-L-AMINO ACID-L-CYSTINE-PEPTIDE CONTAINING AMINO ACID PREPARATIONS FOR ORAL PARENTERAL NUTRITION

[75] Inventors: Peter Stehle; Peter Fürst, both of Stuttgart; Werner Fekl, Röttenbach, all of Fed. Rep. of Germany

[73] Assignee: Pfrimmer + Co. Pharmazeutische Werke Erlangen GmbH + co. KG, Erlangen, Fed. Rep. of Germany

[21] Appl. No.: 228,927

[22] PCT Filed: Oct. 23, 1987

[86] PCT No.: PCT/EP87/00631

§ 371 Date: Jun. 24, 1988

§ 102(e) Date: Jun. 24, 1988

[87] PCT Pub. No.: WO88/03150

PCT Pub. Date: May 5, 1988

[30] Foreign Application Priority Data

Oct. 24, 1986 [DE] Fed. Rep. of Germany ....... 3636334

[51] Int. Cl.$^5$ ........................ A61K 37/02; C07K 5/08; C07K 5/10

[52] U.S. Cl. ...................................... 514/18; 530/330; 530/331

[58] Field of Search .................... 530/331, 330; 514/18

[56] References Cited

U.S. PATENT DOCUMENTS

| | | | |
|---|---|---|---|
| 3,794,633 | 2/1974 | Kamber et al. | 530/336 |
| 3,875,136 | 4/1975 | Kamber | 530/336 |
| 4,258,193 | 3/1981 | Fujii et al. | 530/331 |
| 4,284,624 | 8/1981 | Natarajan et al. | 530/331 |
| 4,325,943 | 4/1982 | Natarajan et al. | 530/331 |
| 4,325,944 | 4/1982 | Natarajan et al. | 530/331 |
| 4,325,945 | 4/1982 | Natarajan et al. | 514/18 |
| 4,427,582 | 1/1984 | Gilvarg et al. | 514/18 |

FOREIGN PATENT DOCUMENTS

| | | |
|---|---|---|
| 0087750 | 2/1984 | European Pat. Off. . |
| 0128249 | 12/1984 | European Pat. Off. . |
| 245033 | 2/1964 | Netherlands . |

OTHER PUBLICATIONS

"Chemistry of Aliphatic Disulfides. XII. Synthesis of Unsymmetrical Open-Chain Cystine Derivatives[1-3]", Richard G. Hiskey et al., Journal of Organic Chemistry, vol. 32 (Jan. 1967), pp. 97–102.

"Amino Acids and Peptides. Part XL. Protection Removable by Electrolytic Reduction: the Use of S-4-Picolyl-L-Cysteine and 0-4-Picolyl-L-Tyrosine in Synthesis", Anthony Gosden et al., Chemical Abstracts, vol. 86, No. 107036u (1977), p. 555.

"A Refinement of the Crystal Structure of N,N'-Diglycyl-L-Cystine Dihydrate", William C. Stallings, Jr., et al., Chemical Abtracts, vol. 85, No. 71026d (1976), p. 564.

"Chromatographic Properties of Peptides of Cystine and Glycine and Some Related Derivatives", Marvin D. Armstrong, Chemical Abstracts, vol. 91, No. 170996a (1979), p. 304.

Primary Examiner—Lester L. Lee
Attorney, Agent, or Firm—Burns, Doane, Swecker & Mathis

[57] ABSTRACT

N-N-bis-L-amino acid-L-cystine- peptides which are suitable as water soluble cystine donors in oral or parenteral nutrition.

8 Claims, 3 Drawing Sheets

N,N'-BIS-L-AMINO ACID-L-CYSTINE-PEPTIDE CONTAINING AMINO ACID PREPARATIONS FOR ORAL PARENTERAL NUTRITION

The sulfur containing amino acid cysteine and its stable dimeric disulfide product cystine, which is formed therefrom readily upon oxidation, do not belong to the classic essential amino acids, but nevertheless cystine is considered an indispensible component in amino acid preparations provided for the nutrition of babies, for chronical uremia, hepatic cirrhosis and of the injured. The reason for the essentiality in said cases is a non-sufficient or completely missing synthesis of cystine from the respective sulfur-containing amino acids methionine and cystine serving as intermediates in the body.

Since in many cases newborn or premature infants as well as patients showing the above syndromes have to be fed intravenously, it is essential to incorporate cystine in adequate amounts into the respective nutritious solutions. However, this is prevented by the very poor solubility of free cystine in water, which is only 0.1 g/l $H_2O$.

A soluble derivative has been provided by the acetylation of cystine, the product being used in small amounts in amino acid preparations. However, this cysteine compound, too, is readily oxidized to the disulfide product in aqueous solution. On the other hand, in contrast to free cystine, this N,N'-bis-acetylcystine has a relatively high solubility in water and therefore stays in solution, which is the reason why it has been tried to use this diacetyated cystine in infusion preparations. However, new studies show unambiguously that acetylated amino acids have a poor utilization in man only and can be used to a small extent only for the synthesis of endogenous protein. Diglycylcystine is known as a soluble cystine compound for a long time and has been used as a substrate for peptidase studies, as the cleavage of this peptide can be readily measured due to the precipitation of insoluble cystine, cf. J. Biol. Chemistry, vol. 128, 241–243 (1939). In spite of an existing need, this cystine peptide has not been used for nutritional purposes in practice so far.

It is further known to transform poorly soluble amino acids as tyrosin and also cystine into very readily water soluble peptides by condensation with the dibasic amino acid lysine. For example, the European Patent specification 87 751 describes the preparation and use of $N^2$-L-cystinyl-$N^6$-L-cystinyl-L-lysine, which is a tripeptide readily soluble in water in spite of its two cystinyl groups, the two cystinyl residues being attached to the two amino groups of the lysine by one of their respective carboxyl groups.

Experiments to provide a simple and inexpensive but also well metabolizable and water soluble cystine peptide by synthesis of a tripeptide from two moles of alanine and one mole of cystine, in which in an analogous way to the known lysine derivatives the amino groups of the alanine molecules are bound to the carboxyl groups of the cystine have shown indeed that this L-cystinyl-bis-L-alanine having the two carboxyl groups of the cystine each bound to the amino group of an alanine, is well soluble in water, however, is unstable upon heat sterilization (121° C.) and results in the formation of other derivatives already after 8 minutes, this leading to a reduction or loss of the bio-availability of the cystine.

Surprisingly, it has now been found that in contrast to this tripeptide N,N'-bis-L-alanyl-L-cystine-peptide as well as, in general, the N,N'-bis-L-amino acid-L-cystine-peptides of the general formula

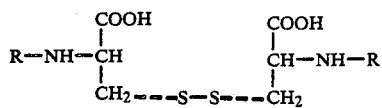

wherein R represents a L-amino acid residue, are not only well soluble in water, but also remain stable upon heat sterilization in aqueous solutions, i.e. are not modified thereby, and in spite of this stability can be readily cleaved and utilized in the body, which renders them well suited as highly bio-available cystine compounds in amino acid and oligopeptide preparations for oral and parenteral nutrition.

Since the composition with respect to the amino acids is identical in the two types of peptides, e.g. in L-cystinyl-bis-alanine and bis-L-alanyl-L-cystine of the invention, the reason for this surprising stability of the one type tris-amino peptides must go back to the different amino acid sequences. The two free amino groups of cystine are spaced very close to each other when the cystine residue is in the N-terminal position. Under thermal stress, this could lead to an intramolecular cyclization under release of ammonia. On the other hand, when cystine is found in the C-terminal position, the free amino groups are at the substituent amino acid residues. Under these conditions a ring formation is almost to be excluded, as the amino groups are spaced apart from each other. A cyclization of the two free carboxyl groups (under release of $CO_2$) upon heating seems not to take place because of the low nucleophilicity of these groups. This is further supported by the findings that all sterilization products formed in the heat treatment of the unstable L-cystinyl-bis-L-alanine absorbs at 254 nm. This means, that the disulfide bonding of the cystine group is not attacked during sterilization. Furthermore, all of the new products formed in the thermal treatment show a high UV absorption at 206 nm, wherefrom it can be concluded that the peptide bonding as such is present unchanged.

From the present results it is to be concluded that a cystine tripeptide having a carboxyl terminal cystine residue has sufficient thermal stability for the sterilization of solutions for parenteral nutrition, independently from the kind of the N-terminal amino acid. This holds true not only for the N,N'-bis-alanyl tripeptide of cystine, but also for analoguous cystine peptides, such as the N,N'-bis-glycyl-L-cystine, which is known for long, as well as the N,N'-bis-L-leucyl-L-cystine, N,N'-bis-L-isoleucyl-L-cystine or N,N'-bis-L-phenylalanyl-L-cystine, which therefore are suited for the use as cystine derivatives in amino acid or oligopeptide preparations for oral or parenteral nutrition according to the invention, the N,N'-bis-L-alanyl-L-cystine being particularly well suited therefor.

The diamino acid-cystine-peptides may be prepared in a usual way by means of the N-carboxyanhydride method (NCA-method), in which the free amino group of S-acetamidomethyl-L-cysteine reacts with the respective N-carboxyanhydride of the amino acid to be attached, analogously to the process described by R. Hirschmann et al. in J. Org. Chem., vol. 32, 3415–3425 (1967); J Am. Chem. Soc., vol. 93, 2746–2755 (1971).

The corresponding cystine peptide is obtained by the subsequent cleaving off of the protective group and oxidation.

For physiological investigation of the in vivo utilization of bis-amino acid cystine-peptides bis-glycyl-L-cystine and bis-L-alanyl-L-cystine were selected as examples and injected into male Wistar-rats in the form of a peptide single injection (50 μmole/100 g bw and 20 μmole/100 g bw respectively, injection volume 0.5–1 ml), by means of a vena cava-catheter within 5 s. The withdrawal of blood (1 ml in herparinized syringes) was 30, 60, 120, 180 and 300 s after application of the peptides. The plasma obtained by centrifugation was subsequently treated with 30% SSA (ratio of sample to SSA 10:1) for precipitation, maintained 1 h at 4° C., and finally centrifuged.

For determination of the bis-glycyl-L-cystine, mono-glycyl-L-cystine, bis-L-alanyl-L-cystine, mono-L-alanyl-L-cystine peptides as well as of the free amino acids glycine, alanine and cystine the precipitated plasma samples were analysed by high pressure liquid chromatography after pre-column derivatization with 5 dimethylaminonaphthaline-1-sulphonylchloride (DANSYL-Cl). The analytical conditions are summarized below:

RP-HPLC after DANSYL-Precolumn Derivatization

Column: Spherisorb ODS 11 3 μm (125×4.6 mm)
Eluent:
(A) 12.5 mM Na-phosphate-buffer of pH 6.6
(B) 40% A; 60% ACN
Flow: 1.2 ml/min
Detection: fluorescence Em 550/Ex 325

(a) Injection of bis-glycine-cysteine=(gly-cys)$_2$

In FIG. 1 the respective peptide/amino acid concentrations measured at the individual sampling times after single injection of (gly-cys)$_2$ (50 μmole/100 g bw) are shown. The concentration of the tripeptide (gly-cys)$_2$ decreases continuously for the time of the experiment, 5 min after injection only about 10% of the values measured after 30 s being present. Expect (gly-cys)$_2$, in all samples the mono-substituted dipeptide gly-(cys)$_2$ (intermediate product from the hydrolytic cleavage of the tripeptide (gly-cys)$_2$ can be detected. Whereas the concentration of this dipeptide remains constant over the first two sampling times, it decreases almost parallel to (gly-cys)$_2$ thereafter.

Already 30 s after injection the concentrations of glycine and cystine have multiplied (gly: 12-fold; (cys)$_2$: 14-fold), as compared to the starting concentrations. Although remaining almost constant at a high level at all times, the curve exhibits two maxima for the glycine concentration at 60 s and 180 s, respectively. This observation could be explained by the stepwise hydrolysis of (gly-cys)$_2$, in which in the first step glycine and the mono-substituted dipeptide gly-(cys)$_2$ are released and in the second phase the dipeptide is cleaved into the amino acids glycine and cystine. It seems that first a rapid cleavage of the tripeptide present takes place and only after decrease of the tripeptide concentration a further hydrolysis of the dipeptide occurs, which is confirmed by the cystine values measured. In contrast to gylcine, the cystine concentration rises continuously until after 5 min after injection and reaches a value that is about 30 times the starting value.

If for a kinetic assessment a two compartment model is used, application of the residual method results in a calculated half-life of 240±89 s (n=5).

Figure 2:
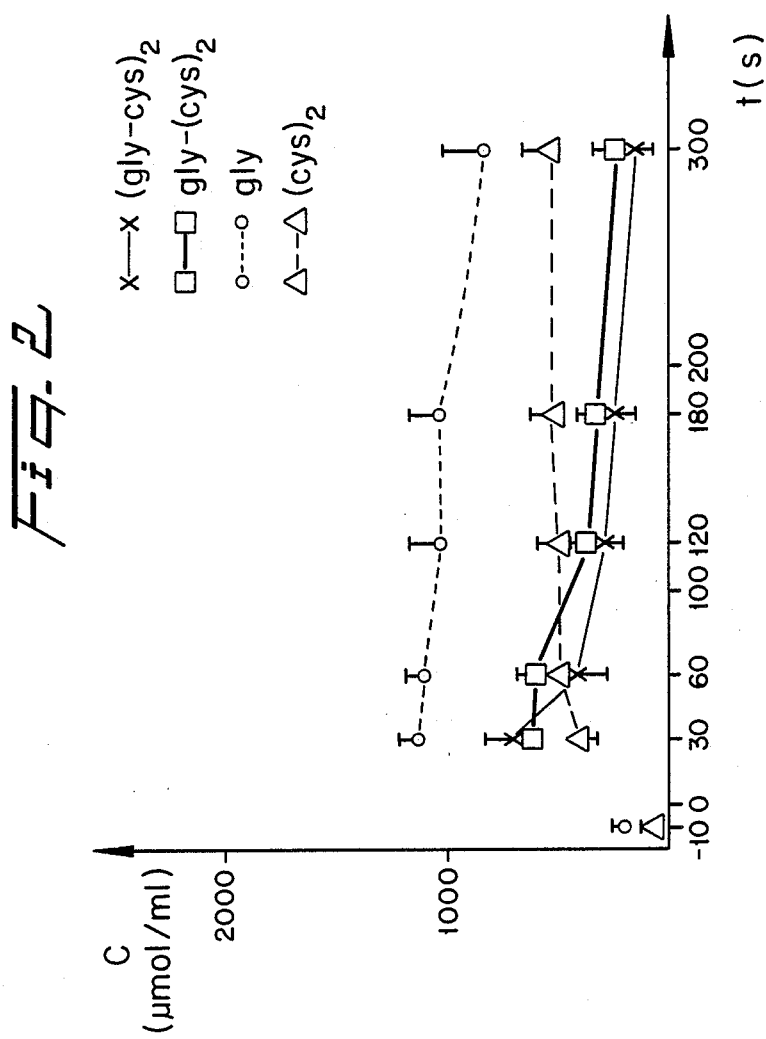

In FIG. 2 the plasma concentrations detected after injection of 20 μmole (gly-cys)$_2$/100 g bw are shown at individual sampling times. Basically, similar courses are observed for concentrations. At the time of the first measurement, the concentrations of the two amino acids glycine and cystine are considerably increased, as compared to the starting point (gly: 5 fold; (cys)$_2$: 10-fold).

Whereas the cystine concentration increases continuously, that of glycine remains relatively constant during the first 180 s and slightly decreases after 300 s. Although the value measured after 180 s is slightly higher than that after 120 s, this cannot be considered a clear second glycine maximum.

It is of interest that already 30 s after injection similar concentrations are obtained for the intermediate product of hydrolysis gly-(cys)$_2$ as for (gly-cys)$_2$. The concentrations of both peptides then decrease continuously to the same extent in the further course.

(b) Injection of Bis-alanyl-cystine=(ala-cys)$_2$

Figure 3:
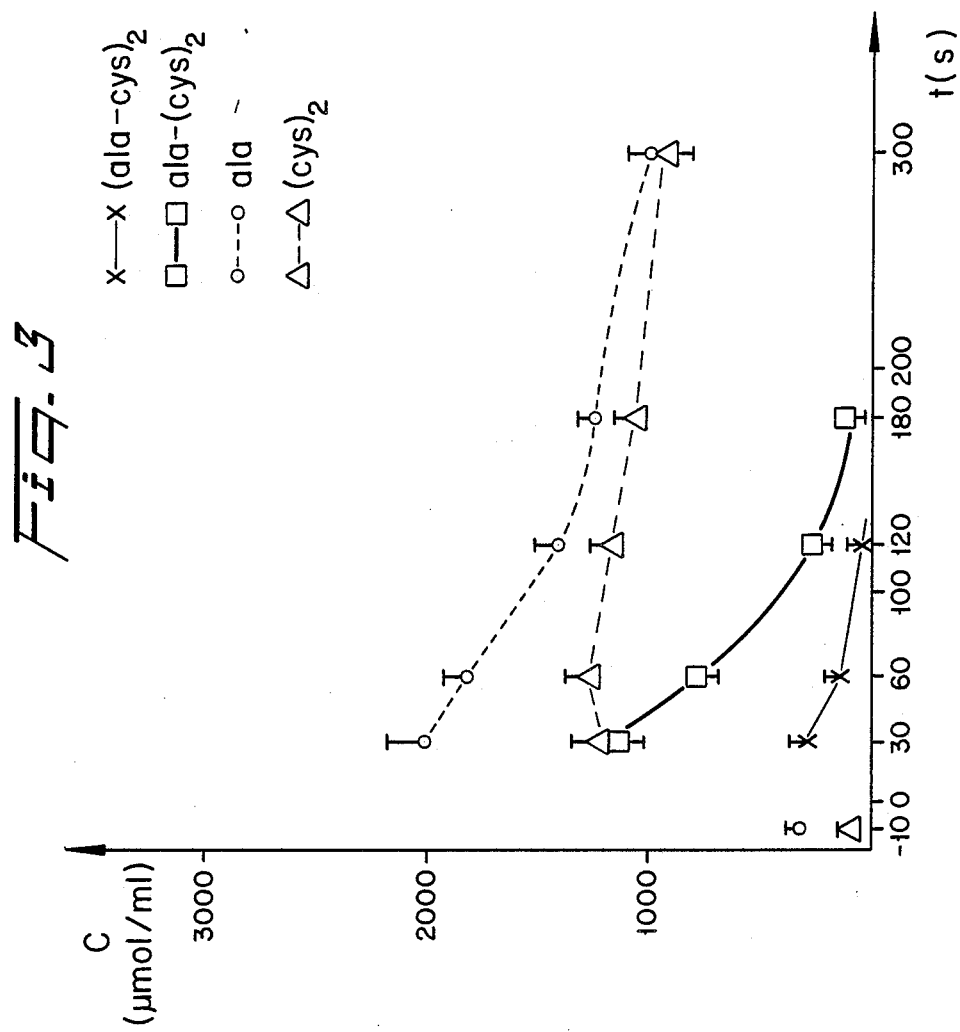

In FIG. 3 the respective peptide/amino acid concentrations measured after injection of (ala-cys)$_2$ (20 μmole/100 g bw) are shown for individual sampling times.

The infused tripeptide (ala-cys)$_2$ could only be detected within the first 2 min in all 6 test animals. Already 180 s after injection (ala-cys)$_2$ could only be detected in one sample in low concentration (about 20 μmole/ml). At the time of the last sampling, (ala-cys)$_2$ could not be detected in any of the animals.

Already 30 s after injection, the concentration of the intermediate hydrolysis product ala-(cys)$_2$ already 30 s was about 5 fold higher than that of the tripeptide (ala-cys)$_2$. In the further course, the concentration of ala-(cys)$_2$ decreased very rapidly. At the end of the test after 300 s, in one test animal only very slight amounts of ala-(cys)$_2$ could be detected. During the whole measuring time the concentration of alanine, which at the beginning was almost 7 times the starting level, decreased continuously. After 300 s a level corresponding to 3 times the starting level was reached. The maximum cystine concentration (23 times of the starting concentration) was measured after 60 s. During the time of measurement, the concentration of this amino acid decreased slowly, but steadily.

Because of the very fast peptide elimination it was not possible, to calculate a half life based on the measured data, as for (gly-cys)$_2$. From the data present, it can only be concluded that the plasma half-life is less than 2 min.

The results obtained with the two bis-amino acid-cystine peptides to be used according to the invention clearly show that both (gly-cys)$_2$ and (ala-cys)$_2$ are rapidly cleared from the plasma after single injection. The occurrance of the respective mono substituted dipeptides and the fast increase in concentration of the corresponding free amino acids cystine and glycine or alanine as compared to the starting levels, allow the conclusion that the elimination of the peptides predominantly results from a stepwise hydrolytic clevage of (gly-cys)$_2$ or (ala-cys)$_2$, respectively. The high plasma concentrations of the mono substituted peptides may be interpreted as an indication for a hydrolysis in the plasma or at the plasma membrane.

As can be seen from FIG. 2 and 3, the tripeptide (ala-cys)$_2$ is cleaved to the free amino acids considerably faster than (gly-cys)$_2$. Whereas 30 s after injection of (gly-cys)$_2$ (20 μmol/100 g bw) 655 μmol/ml tripeptide could be detected, after respective single injection of (ala-cys)₂ only 280 μmole/ml could be determined in the plasma. Though because of the fast hydrolysis of (ala-cys)₂ no pharmacokinetic assessment was possible, the half-life of (ala-cys)₂ is obviously considerably shorter than that of (gly-cys)₂.

The more rapid in vivo-utilization of (ala-cys)₂ is also reflected in the amino acid concentration. Whereas after application ion of (gly-cys)₂ the concentration of glycin remains at a uniform level within the time of assessment and that of cystine continuously increases (FIG. 3) the concentrations of alanine and cystine decrease after injection of (ala-cys)₂ more clearly up to the time of the last collection, maxima having been observed already after 30 s (alanine) and 60 s (cystine), respectively.

The in vivo tests for the utilization of cystine containing tripeptides intravenously applied according to the invention prove the rapid absorption and subsequent hydrolysis of the peptides (gly-cys)₂ and (ala-cys)₂.

Since the present results lead to the conclusion that the peptides are cleaved either in the plasma or at the plasma membrane, the considerably faster utilization of (ala-cys)₂ and the increased elimination from the plasma by absorption into the cells connected therewith represents an advantage of the alanine peptide in comparison to (gly-cys)₂. Although both tripeptides are utilized in vivo and therefore represent useful cystine substrates for parenteral and oral nutrition, bis-L-alanyl-L-cystine-peptide may be considered a preferred source of cystine. However, the higher bis-amino acid-cystine-peptides, as e.g. bis-L-leucyl-L-cystine peptide, bis-isoleucyl-L-cystine-peptide or bis-L-phenylalanyl-L-cystine-peptide, are also well suited for the rapid supply of cystine for endogenous peptide synthesis, in the case of the use of essential amino acids for the cystine peptides, said amino acids to be supplied to the body being available for the body together with the cystine.

The N,N'-bis-L-amino acid-L-cystine-peptides of the general formula

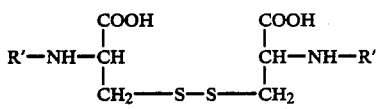

wherein R' represents an amino acid residue with 3 or more carbon atoms, are novel compounds and therefore represent an object of the invention. As already mentioned, they may be prepared by the N-carboxyanhydride method from cysteine and subsequent oxidation. They are stable to heat and in spite of this are rapidly cleaved in the body or in the cells by respective peptidases, so that the cystine important of the synthesis for endogenous peptides is available in sufficient amounts.

EXAMPLE 1

Synthesis of N,N'-bis-L-alanyl-L-cystine according to the NCA-method 4 mmole (0.91 g) S-acetamidomethyl-L-cysteine (S-acm-cys) are reacted with 4.5 mmol (0.52 g) alanine-NCA in aqueous solution (250 cm³) at a pH of 10.2 and 0° C. The resulting ala-S(acm)cys is isolated by gel chromatography and the AMC-protective group cleaved off with Hg(CH₃COO)₂ at a pH of 4.0 thereafter. After precipitation of the Hg-salt with H₂S and subsequent filtration at pH 7, oxidation to the cystine tripeptide is carried out. After gel chromatographic work up of the oxidized charge the N,N'-bis-L-alanyl-L-cystine of a mp. (decomposition) 195°–200° C. is isolated.

EXAMPLE 2

Synthesis of N,N'-bis-L-isoleucyl-L-cystine according to the active ester method 400 μmole (91.5 mg) S-acetamidomethyl-L-cysteine HCl are dissolved in 4 ml 0.1 KCl, transferred to a thermoregulated reactor (40° C.) and adjusted to a pH of 9.2 with NaOH. The reaction is started by addition of 200 μmol (72.5 mg) carbobenzoxy-L-isoleucine-hydroxysuccinimidester dissolved in DMSO. The pH is kept constant by continuous controlled addition of NaOH. After completion of the reaction (4 h) the charge is worked up by gel chromatography to isolate the peptide. Thereafter, the carbobenzoxy protective group is cleaved off by catalytic hydrogenation in an aqueous organic solvent mixture in the presence of a palladium-on-carbon catalyst in a manner known per se. After preparation of the solvent, the acetamido protective group is cleaved off, as described in example 1, and subsequently oxidation to the cystine tripeptide is carried out. After gel chromatographic purification N,N'-bis-L-isoleucyl-L-cystine of mp. (decomposition) 209°–213° C. is isolated.

EXAMPLE 3

Synthesis of N,N'-bis-L-phenylalanyl-L-cystine according to the active ester method 400 μmole (91.5 mg) acetamidomethyl-L-cysteine Cl are reacted with 200 μmole (79.3 mg) carbobenzoxy-L-phenylalanine-hydrosuccinidester, as described in Example 2. After work-up, cleaving off of the protective groups and oxidation (as described in Example 2) N,N'-bis-L-phenylalanyl-cystine of mp. (decomposition) 217°–220° C. is obtained.

Sterilization tests

Starting from a stock solution of the tripeptide of the invention so obtained (2 mmol/l in tris-buffer) solutions having pH-values of 5.5, 6.5, 7.5 and 8.5 were prepared by addition of 0.1 N HCL or KOH, respectively. Thereafter 0.1 ml each of these solutions were filled into ampoules purified with chromosulfuric acid, met sealed under vacuum and sterilized over 8, 12, 15 or 30 min, respectively.

Further respective solution of the cystinyl-bis-alanine-tripeptide were prepared and treated analogeously.

The stock solutions as well as the sterilized samples were analysized by means of capillary-isotachophoreses and HPLC. In contrast to L-cystinyl-bis-alanine-tripeptide the N,N'-bis-L-amino acid-L-cystine peptides of the invention remained practically unchanged even after heating over 30 min, which shows their surprising stability under heat sterilization conditions. Therefore, said tripeptides are not only suitable for oral preparations, but also and in particular for the preparation of parenteral infusion solutions.

The following examples show infusion solutions for parenteral applications.

EXAMPLE 4

| Peptides and amino acids | g/1000 ml |
|---|---|
| (ala-cys)₂ | 4.8 |
| gly-tyr[(1)] | 6.6 |

-continued

| Peptides and amino acids | g/1000 ml |
|---|---|
| L-histidine | 5.5 |
| L-isoleucine | 7.0 |
| L-leucine | 11.0 |
| L-lysine-monoacetate | 7.7 |
| L-methionine | 9.0 |
| L-phenylalanine | 6.0 |
| L-threonine | 5.0 |
| L-tryptophane | 2.5 |
| L-valine | 8.0 |

[1] Glycyl-L-tyrosine This dipeptide contains L-tyrosine in readily soluble form.

EXAMPLE 5

| Peptides and amino acids | g/1000 ml |
|---|---|
| ala-gln[1] | 17.8 |
| L-isoleucine | 2.1 |
| L-leucine | 2.9 |
| L-lysine-acetate | 4.37 |
| L-methionine | 1.80 |
| L-threonine | 2.70 |
| L-tryptophane | 1.00 |
| L-valine | 2.30 |
| L-arginine | 7.00 |
| L-histidine | 1.75 |
| L-alanine | 0.7 |
| L-glutamic acid | 5.00 |
| glycine | 6.4 |
| L-proline | 7.0 |
| L-serine | 6.2 |
| (phe-cys)2 | 4.0 |
| gly-tyr[2] | 2.6 |
| potassium hydroxide | 1.96 |
| sodium chloride | 2.57 |
| calciumglycerophosphate-dihydrate | 0.49 |
| magnesium chloride | 0.61 |
| sodiumglycerophosphate | 5.51 |
| potassium chloride | 0.37 |

[1] L-alanyl-L-glutamine
[2] 2-glycyl-L-tyrosine The two dipeptides contain L-gutamine and L-tyrosine, respectively, in stable or readiy soluble form.

EXAMPLE 6

| Peptides and amino acids | g/1000 ml |
|---|---|
| ala-gln[1] | 1.5 |
| L-isoleucine | 7.60 |
| L-leucine | 8.50 |
| L-lysine-monomalate | 7.67 |
| L-methionine | 0.25 |
| L-phenylalanine | 0.10 |
| L-threonine | 1.20 |
| L-tryptophane | 0.10 |
| L-valine | 6.40 |
| L-arginine | 4.90 |
| L-histidine | 0.60 |
| L-ornithine-L-aspartate | 8.03 |
| L-alanine | 1.50 |
| L-glutamic acid | 1.00 |
| glycine | 0.50 |
| L-proline | 1.20 |
| L-serine | 1.75 |
| (gly-cys)2 | 0.20 |
| tyr-lys (tyr)[2] | 0.20 |
| sodiumglycerophosphate-pentahydrate | 4.52 |
| magnesium chloride | 1.02 |

-continued

| Peptides and amino acids | g/1000 ml |
|---|---|
| potassium chloride | 1.34 |

[1] L-alanyl-L-glutamine
[2] N2-L-tyrosinyl-N6-L-tyrosinyl-L-lysine
The two peptides contain L-glutamine and L-tyrosine, respectively, in stable or readily soluble form.

EXAMPLE 7

| Peptides and amino acids | g/1000 ml |
|---|---|
| (ala-cys)2 | 4.8 |
| tyr-lys (tyr)[1] | 6.1 |
| L-isoleucine | 6.0 |
| L-leucine | 9.4 |
| L-lysine-monoacetate | 4.23 |
| L-methionine | 6.5 |
| L-phenylalanine | 6.0 |
| L-threonine | 4.5 |
| L-tryptophane | 2.2 |
| L-valine | 7.0 |
| L-histidine | 4.5 |
| L-alanine | 7.0 |
| L-arginine | 5.0 |
| L-glutamic acid | 4.5 |
| glycine | 2.0 |
| L-serine | 2.5 |
| L-propline | 5.0 |
| gly-gln[2] | 8.3 |

[1] N2-L-tyrosinyl-N6-L-tyrosinyl-L-lysine
[2] glycyl-L-glutamine
The two peptides contain L-glutamine and L-tyrosine respectively, in stable or readily soluble form.

What is claimed is:

1. A method for providing oral or parenteral nutrition, said method comprising administering to a human in need of such nutrition a sufficient amount to effectively treat nutritional deficiencies of a peptide, wherein said peptide is N,N'-bis-L-alanyl-L-cystine-peptide, N,N'-bis-L-leucyl-L-cystine-peptide, N,N'-bis-L-isoleucyl-L-cystine-peptide, or a mixture thereof.

2. An amino acid peptide comprising N,N'-bis-L-alanyl-L-cystine-peptide or N,N'-bis-L-leucyl-1-cystine-peptide.

3. N,N'-bis-L-alanyl-L-cystine-peptide.

4. N,N'-bis-L-leucyl-L-cystine-peptide.

5. N,N'-bis-L-leucyl-isoleucyl-L-cystine-peptide.

6. An amino acid composition for oral or parenteral nutrition, said composition comprising N,N'-bis-L-alanyl-L-cystine-peptide, N,N'-bis-L-leucyl-L-cystine-peptide or N,N'-bis-L-isoleucyl-L-cystine-peptide or a mixture thereof and a pharmaceutically acceptable carrier thereof.

7. A method for treating chronic uremia or hepatic cirrhosis, said method comprising administering to a human in need of such treatment a sufficient amount to effectively treat chromic uremia or hepatitic cirrhosis or a peptide, wherein said peptide is N,N'-bis-L-alanyl-L-cystine-peptide, N,N'-bis-L-leucyl-L-cystine-peptide, N,N'-bis-L-isoleucyl-L-cystine-peptide, or a mixture thereof.

8. A method for providing nutrition to an injured patient, said method comprising administering to a human in need of such nutrition, a sufficient amount to effectively provide nutrition to said injured patient of a peptide, wherein said petpide is N,N'-bis-L-alanyl-L-cystine-peptide, N,N'-bis-L-leucyl-L-cystine-peptide, N,N'-bis-L-isoleucyl-L-cystine-peptide or a mixture thereof.

* * * * *